United States Patent [19]

Shibata et al.

[11] 3,958,937
[45] May 25, 1976

[54] METHOD AND APPARATUS FOR DETERMINING TOTAL OXYGEN DEMAND OF COMBUSTIBLE MATERIALS IN AQUEOUS DISPERSION

[75] Inventors: Yoshiki Shibata, Otsu; Hisami Fujino, Shiga; Sigeki Harano; Hideo Kakigami, both of Otsu, all of Japan

[73] Assignee: Toray Industries, Inc., Tokyo, Japan

[22] Filed: June 4, 1974

[21] Appl. No.: 476,410

[30] Foreign Application Priority Data
June 7, 1973  Japan.............................. 48-63388
June 13, 1973  Japan.............................. 48-65810

[52] U.S. Cl..................... 23/230 PC; 23/253 PC; 204/195 S; 204/195 IT
[51] Int. Cl.²............. G01N 27/26; G01N 31/10; G01N 31/12; G01N 33/18
[58] Field of Search............... 23/230 PC, 253 PC; 204/195 S

[56] References Cited
UNITED STATES PATENTS

| | | | |
|---|---|---|---|
| 3,560,156 | 2/1971 | Teal et al...................... | 23/230 PC |
| 3,679,364 | 7/1972 | Teal et al...................... | 23/230 PC |
| 3,784,359 | 1/1974 | Parth............................ | 23/230 PCX |
| 3,791,937 | 2/1974 | Besson et al................. | 204/195 SX |
| 3,819,499 | 6/1974 | Hoogeveen et al.......... | 204/195 S |

OTHER PUBLICATIONS
J. T. Clerc et al, Microchemical Journal, vol. 7 pp. 422–436 (1963).

*Primary Examiner*—Joseph Scovronek

[57] ABSTRACT

A method and an apparatus are provided for determining the total oxygen demand of combustible materials in an aqueous dispersion.

In the first step, a feed gas stream composed of an inert gas containing oxygen is continuously supplied at a constant rate to a combustion conduit having a porous catalyst bed within a combustion zone which is heated at a combustion supporting temperature and an effluent gas from the combustion conduit is supplied to an oxygen detector. In the second step, by means of a bypass the flow rate of the feed gas stream is decreased to a value lower than that of the first step. In the third step, a small sample of the combustible material in an aqueous dispersion is injected into the combustion supporting feed gas stream in advance of the catalyst bed within the combustion zone. As the sample is introduced into the combustion conduit, the combustible materials in the aqueous dispersion are burned. After prosecution of this third step, the flow rate of the feed gas stream is increased again to the same value as in the first step. An electrical signal is generated corresponding to the total oxygen demand for burning the combustible materials.

14 Claims, 10 Drawing Figures

METHOD AND APPARATUS FOR DETERMINING TOTAL OXYGEN DEMAND OF COMBUSTIBLE MATERIALS IN AQUEOUS DISPERSION

BACKGROUND OF THE INVENTION

Determination of the total oxygen demand of combustible materials in an aqueous dispersion has been useful in the field of pollution control. Water pollution control has been a long standing problem and is ever increasing in importance as pollution in various industries continues to grow in relation to natural water resources.

A known method for determining the total oxygen demand of combustible materials in an aqueous dispersion, which is described in the specification of U.S. Pat. No. 3,560,156 may be referred to as the "conventional method" of making this determination.

Because this conventional method is carried out by injection and combustion of a sample while a feed gas stream is flowing in a combustion zone at a high rate of several centimeters per second, this conventional method has various deficiencies. These include:

1. The entire sample must be injected into the combustion zone simultaneously and substantially instantaneously. When this condition is not satisfied, the peak of the measured value as indicated by the output electrical signal of the oxygen detector indicates a value that is lower than the actual value, or at least two peaks appear, or the peak loses its sharpness and widens considerably, and it is not possible to make precise measurements.

2. The contact time between the sample and the catalyst is very short. Therefore, the available combustion time is limited, which means that the unburned sample remains in the combustion zone. This makes it impossible to obtain precision measurements. Moreover, the catalyst or combustion conduit is unnecessarily contaminated.

3. In order to carry out combustion of the sample substantially instantaneously, the temperature of the combustion zone must be quite high, which not only requires increased manufacturing and running costs of the apparatus, but also shortens the lives of the combustion conduit and of the heating furnace as well.

Accordingly, a primary object of the present invention is to provide a method and apparatus for measuring the total oxygen demand which overcomes the deficiencies of conventional methods and drastically improves upon the conditions of simultaneous, momentary injection of the entire sample which has been an indispensable condition of the conventional method.

Another object of the present invention is to provide a method and an apparatus for measuring the total oxygen demand of combustible materials which method is capable of drastically increasing the combustion ratio (oxidation ratio) of the sample.

A third object of the present invention is to provide a method and apparatus for measuring the total oxygen demand of combustible materials, which method is capable of drastically reducing manufacturing and operating costs.

Other objects of the present invention will become clear from the following explanation.

BRIEF DESCRIPTION OF THE DRAWINGS

FIG. 7 is a graph showing the relationship between the seal time of the combustion conduit after injecting the sample and the output of the oxygen detector. FIG. 8 is a graph showing the relationship between the total oxygen demand of different samples and the output of the oxygen detector when the seal time of the combustion conduit after injecting the samples was 60 seconds.

FIG. 9 is a graph showing the relationship between the seal time of the combustion conduit after injecting samples and the output of the oxygen detector. FIG. 10 is a graph showing the relationship between the total oxygen demand of different samples and the output of the oxygen detector when the seal time of the combustion conduit after injecting the samples was 90 seconds.

DESCRIPTION OF THE PREFERRED EMBODIMENTS

The following terms will be used in the specification, as defined herein.

"Combustible materials" refers to materials which burn; which can be reacted chemically with oxygen to form oxides under heating conditions.

"Total Oxygen Demand" (abbreviated as "TOD") is the amount of oxygen required when the combustible materials in an aqueous dispersion burn in the presence of an oxygen-containing feed gas stream.

The present invention basically includes several steps:

a. supplying a feed gas stream composed of an inert gas containing oxygen at a substantially constant rate into a combustion conduit in a combustion zone which is heated at a combustion supporting temperature; the feed gas stream flows through a combustion supporting catalyst bed in the combustion zone into a detector which determines the concentration of oxygen, b. decreasing a flow rate of the feed gas stream to a value below that of step (a), c. injecting a small amount of an aqueous dispersion of combustible materials into the combustion zone upstream of the catalyst bed, whereby the combustible materials are burned, and d. again increasing the flow rate of the feed gas stream to that of step (a), whereby an electrical signal corresponding to the total oxygen demand for burning the combustible materials is generated.

The expression "decreasing the flow rate" as referred to in this description means, as will be mentioned later, providing a flow rate which is less than 1/5, preferably less than 1/10 of the initial flow rate. The flow rate may even be substantially zero.

Figure 1:
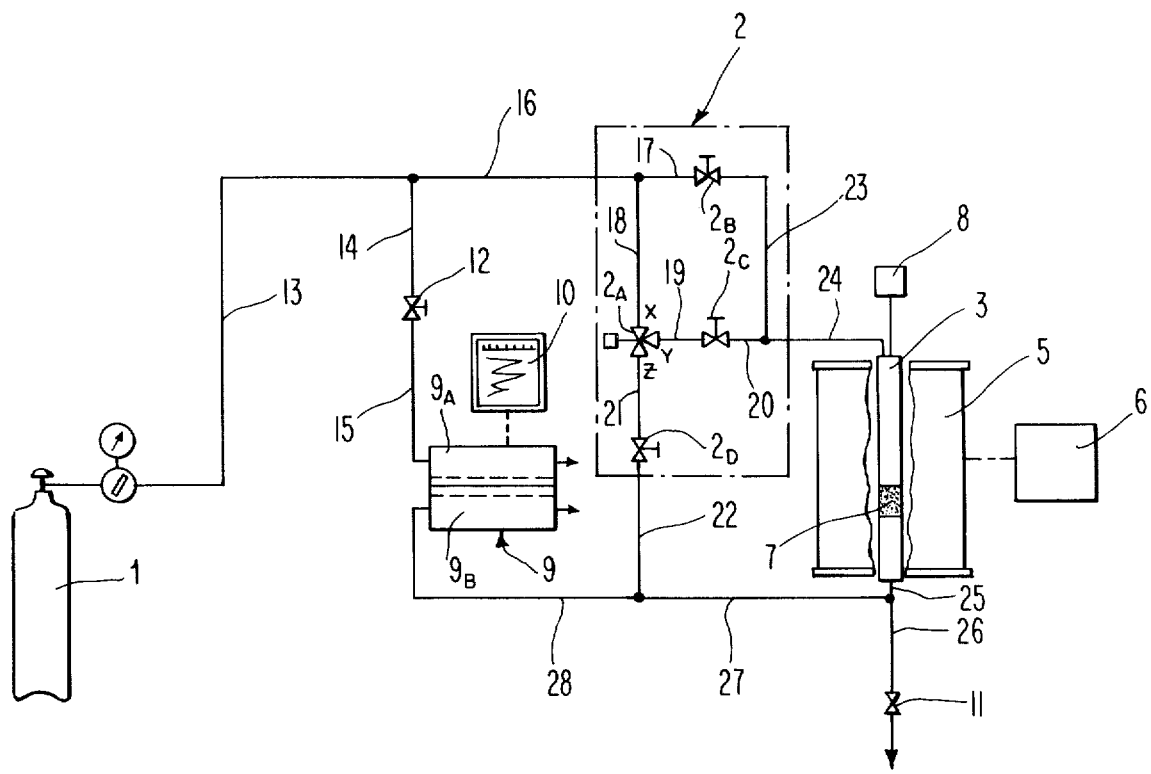
FIG. 1 is a flow diagram showing one form of apparatus for measuring the total oxygen demand of combustible materials in an aqueous dispersion according to the present invention.

An important embodiment of the method and the apparatus of the present invention will now be explained by reference to FIG. 1. In FIG. 1, the basic components comprise a compressed gas tank 1, flow regulators 2A, 2B, 2C, 2D, a combustion conduit 3 heated by an electric furnace 5, a temperature controller 6 for the furnace, a porous catalyst bed 7, a sample injector 8, a continuous detector 9, 9A, 9B, for determining the difference in concentration of oxygen, a recorder 10, valves 11 and 12 and sections 13 – 28 of connecting tubing.

In FIG. 1, a feed gas stream composed of an inert gas containing oxygen is supplied from the tank 1 into the feed tubing 13. This feed gas stream is divided into two parts. One part passes through the tubing 14, in which it is controlled to a predetermined flow rate by the control valve 12, passes through the tubing 15, and is introduced to a first flow path 9A of the continuous detector 9, passes through this first flow path 9A, and is discharged into the atmosphere. The other part of the divided feed gas stream passes through the tubing 16 into the flow regulator 2, which consists of a three-way magnetic valve 2A and three valves 2B, 2C and 2D, which control the flow of the feed gas stream (namely, its flow rate) for introducing into the combustion conduit 3.

The feed gas stream leaving the flow regulator 2 is introduced into the combustion conduit 3 after passing through the tubing 24 and is introduced into the second flow path 9B of the continuous detector 9 after passing through the tubes 25, 26 and 28. The output electrical signal of the continuous detector 9 is recorded by the recorder 10.

The temperature of the combustion conduit 3 is controlled to an optimum combustion supporting temperature by the electric furnace 5 and the temperature controller 6. Above the combustion conduit 3 is a sample injector 8 for injecting an aqueous dispersion of combustible material (hereinafter referred to as the "sample"). Below the combustion conduit 3 is a valve 11 for a discharge drain entered via tubes 25 and 26.

In accordance with the method illustrated in FIG. 1, the feed gas stream inside the tubing 16 passes through two flow paths:

a. the tube 17 — valve 2B — tube 23 — tube 24 (hereinafter referred to as the "first flow path") and b. a flow path through tube 18 — ports X and Y of the three-way valve 2A — tube 19 — valve 2C — tube 20 — tube 24 (hereinafter referred to as the "second flow path").

The flow rate of the feed gas stream is controlled by the valves 2B and 2C. When the flow rate in flow path (a) is designated ($F_1$) and the flow rate in flow path (b) is called ($F_2$), the relationship ($F_1 < F_2$) is maintained.

At this time, the space between the ports X and Z of the three-way valve 2A is closed. Therefore, the feed gas stream does not flow through the flow path which includes tube 21 — valve 2D — tube 22 (hereinafter referred to as the "third flow path").

As mentioned above, in the first step, the feed gas stream ($F_1 + F_2$) flows into the combustion conduit 3.

Next, the three-way valve 2A is adjusted to communicate through its ports X and Z and at the same time to close the connection through X and Y.

Accordingly, the feed gas stream introduced into the combustion conduit 3 becomes the feed gas stream passing through the flow path (a) only (the first flow path).

At this time, in said third flow path, a certain flow rate is established and adjusted by the valve 2D of the feed gas stream (hereinafter referred to as "$F_3$"), which joins the feed gas stream coming from flow path ($F_1$) at the point of contact with the tubing 27.

At this time, when the flow rate in the third flow path is so set up as to make ($F_3 = F_2$), even when the first step is switched over to the second step, by closing off flow through ports X and Y of three-way valve $2_A$ and opening up flow through ports X and Z, the total flow rate of the feed gas stream introduced into the second flow path 9B of the continuous detector 9 does not change.

As mentioned above, in the second step, (flow through 24 and 22) the flow rate of the feed gas stream flowing in the combustion conduit 3 decreases with respect to that in the first step by ($F_2$).

In proceeding with such second step, a small portion of the sample is injected by sample injector 8 into the feed gas stream in the combustion conduit 3, and upstream of the catalyst bed 7. Combustible material that is contained in the injected sample burns under the influence of the catalytic action of the catalyst bed 7, consuming oxygen in an amount corresponding to the TOD of the sample from the feed gas stream. At this time, the flow rate of the feed gas stream passing through the combustion conduit 3 ($F_1$) is so set that an optimum combustion reaction is carried out. It is necessary to determine the time for which the feed gas stream is maintained in a manner to perform the second step so that the feed gas stream does not flow out downstream of the point of contact of the tubes 27 and 22.

In the third step, the feed gas stream is returned to the setting for the first step by actuating the three-way valve 2A of the flow regulator 2 and introduced in a flow rate of ($F_1 + F_2$) to the second flow path 9B of the continuous detector 9. Then, an electrical signal corresponding to the TOD of the sample is generated in the continuous detector 9 and recorded in the recorder 10.

By comparing this electrical signal with readings prepared in advance from known samples, it is possible to determine the TOD of an unknown sample.

With reference to the aforementioned first embodiment, a more detailed explanation will be made.

The sample to be introduced into the feed gas stream may either be introduced in the liquid state or may be evaporated in advance and introduced in the vapor state.

The continuous detector 9 consists of a solid electrolyte tube capable of conducting electricity purely by means of oxygen ions, and two gas flow paths. It gives rise to an electromotive force according to Nernst's relation, depending upon the difference of concentration of oxygen introduced into the first and second flow paths 9A and 9B.

Now, when the concentration of oxygen in the feed gas stream is sufficiently large, for example more than about 10 times the maximum value of the TOD to be determined, the ratio of the concentration of oxygen in the first and second flow paths approaches 1 and it is possible directly to obtain an electrical output signal from the continuous detector 9 corresponding to the difference in the concentration of oxygen.

Several methods of supplying the feed gas stream are available, including continuously mixing an inert gas and oxygen at a constant ratio, a method using a premixed gas tank obtained by combining an inert gas and oxygen at a constant ratio in advance of filling the gas bomb under pressure, a method by use of electrolysis and a method utilizing permeation and diffusion of oxygen through a porous partition, using a silicone rubber tube, for example. Adoption of a system employing a mixed gas is advantageous in that stability and uniformity of the gas stream as well as the exact desired concentration of oxygen are obtained. However, such a system also has a shortcoming in that the tank of mixed gas is very expensive. From the viewpoint of economy and uniformity, however, controlling the concentration of oxygen in the feed gas stream by utilizing permeation and diffusion through a porous partition is advantageous and is preferred for these reasons. However, by this method, a 10% by volume concentration is at best obtained; a greater concentration is difficult to achieve.

Any gas which is essentially inert may be used as a feed gas. However, nitrogen is economically advantageous as compared with helium and argon. By utilizing a continuous detector 9 for determining the difference of concentration of the oxygen between two feed gas streams, it becomes possible to use the air as it exists in the natural world, which is economically very advantageous.

As to the concentration of oxygen in the feed gas stream, it is basically sufficient that enough oxygen be contained for combustion of the sample. However, it is appropriate to determine the concentration of the oxygen by taking into account the range of TOD, the characteristics of the detector and the economical availability of a feed gas stream containing a predetermined amount of oxygen.

The TODs of various waste differ somewhat, depending upon the water quality. It is less than about 1,000 ppm in many cases and the highest TOD may be considered less than several tens of thousands ppm. When a TOD of about 0.1 ppm can be determined as a lower limit of concentration, almost all objectives of the invention may be achieved.

In addition, an oxygen concentration cell comprising a solid electrolyte partition adapted to a continuous detector has very high detection sensitivity, is readily responsive and is capable of determining the concentration of oxygen in a broad range, from a zone of low concentration of oxygen less than 1 ppm to a zone of high concentration of oxygen which approaches 100%. Moreover, it is capable of detecting and determining a fine change of about 1/10,000 of the concentration of oxygen.

When a decision is made from the foregoing as to the method of supplying the feed gas stream, the concentration of oxygen in the feed gas stream may be about 10 ppm – 10% by volume, generally not more than about 1,000 ppm. However, when analyzing a sample having a high TOD of more than about 100 – 1,000 ppm, it is economically more advantageous to use ordinary air as the feed gas stream.

The porous catalyst bed is prepared by packing one or more catalysts in a bed, in which the catalyst is held by asbestos, glass fibers or quartz fibers as occasion demands. In such case, the catalyst is packed to allow sufficient space so that it does not impose a large resistance to the flow of the feed gas stream. As the catalyst, platinum, cobalt, nickel, silica gel, asbestos, palladium, rhodium or quartz fibers may be used. The temperature of the combustion conduit may vary depending upon the kind of catalyst used and the duration of the second step, which will be mentioned later.

It is preferred, but not absolutely necessary, to keep the following parameters constant; the amount of sample introduced into the gas stream, the combustion temperature, the flow rate of the feed gas stream, and the concentration of the oxygen in the feed gas stream.

Figure 2:
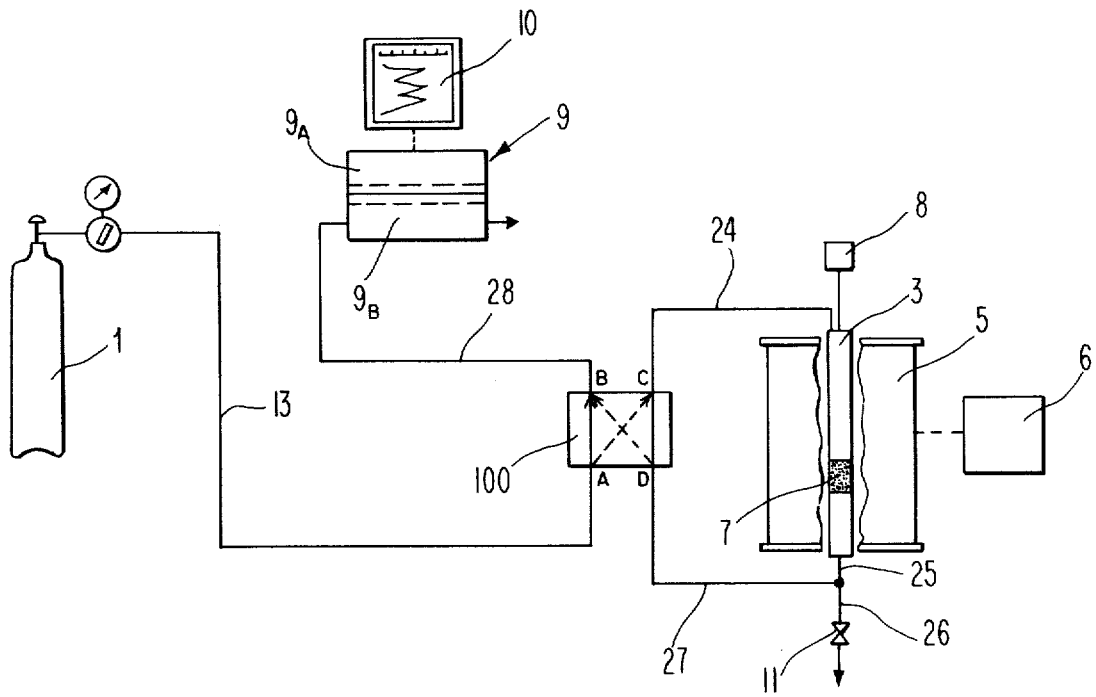
FIG. 2 is a flow diagram showing another embodiment of the present invention.

Next, an explanation will be made with reference to another embodiment of the present invention as represented in FIG. 2. As will be apparent, the main differences between this second embodiment and the first embodiment consist in completely isolating the combustion conduit from the feed gas flow stream by a flow path switchover device and keeping the conduit sealed.

In the following embodiment, parts which are the same as those in FIG. 1 have been given the same reference numbers, and the functional effects of such parts are the same.

In FIG. 2, a feed gas stream composed of an inert gas containing oxygen is supplied from a tank 1 and introduced into a flow path switchover device 100 via tubing 13. The flow path switchover device 100 consists of a four-way valve having ports A, B, C and D, having capacity to switch over the feed gas stream to form a flow path A — C, D—CB (as shown by dotted lines) and a flow path A — B, D — C (shown by solid lines).

In the first step, the feed gas stream introduced into the flow path switchover device 100 is passed through the ports A — C, and introduced into combustion conduit 3 via tubing 24. The feed gas stream flows through the catalyst bed 7 for supporting combustion of combustible materials and is introduced into the second flow path 9B of continuous detector 9 via tubings 25, and 27, ports D — B of the flow path switchover device 100 and tubing 28, and is discharged into the atmosphere. The tubing 25 at the exit of combustion conduit 3 has branch tubing 26, fitted with a valve 11 for discharging to the drain.

When the flow path switchover device 100 is actuated to switch over the feed gas stream to its alternate position, the feed gas stream supplied from the tank 1 flows into the oxygen detector 9 via tubing 13, ports A — B of the flow path switchover device 100 and tubing 28, and is discharged into the atmosphere. At this time, the supply of fresh feed gas to the combustion conduit 3 is stopped and the combustion conduit 3 is sealed by the tubing 24, 25, 26, 27, valve 11 and ports D — C of the flow path switchover device 100.

In such second step, a small amount of sample is injected into the combustion conduit 3 by a sample injector 8. Combustible materials in the injected sample react with oxygen contained in the feed gas inside the combustion conduit 3 in the presence of the catalytic action of the catalyst bed 7, consuming oxygen in an amount corresponding to the TOD of the sample.

Thereafter, by actuating the flow path switchover device 100 again to return the feed gas stream to the first setting, the gas inside the combustion conduit 3 participating in the combustion reaction is carried into the second flow path 9B of the continuous detector 9 via tubing 27, ports D — B of the flow path switchover device 100 and tubing 28 and is converted to an electrical signal corresponding to the oxygen concentration in the feed gas stream, namely, the TOD, and this electrical signal is recorded by recorder 10.

As will be apparent from a study of this embodiment of the invention, the aforementioned objects of the present invention may be achieved even when the continuous detector 9 is not of the concentration difference type, but is one in which a single flow path is used.

Figure 3:
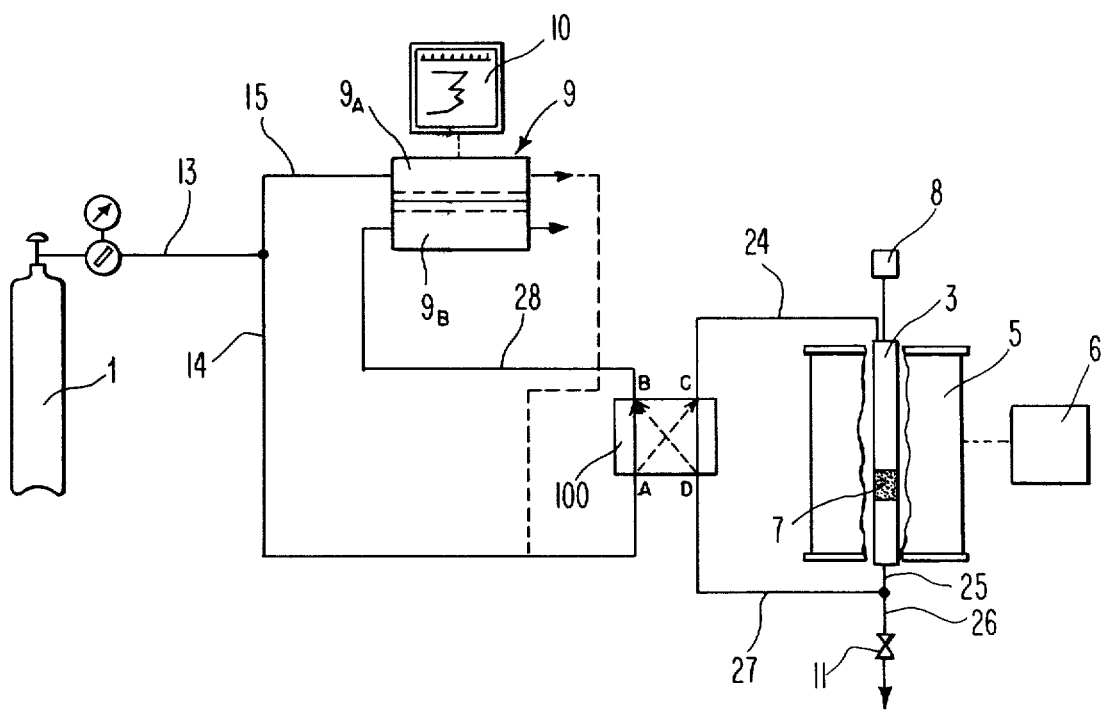
FIG. 3 is a flow diagram showing other embodiments of the present invention.

Next, an explanation will be made with reference to a third embodiment of the present invention, as illustrated in FIG. 3 of the drawings.

In FIG. 3, a feed gas stream composed of an inert gas containing oxygen is supplied from a tank 1 and divided into two branches: tubing 15 and tubing 14 at the tip of tubing 13. The feed gas stream supplied from the tubing 15 passes through the first flow path 9A of a continuous detector 9 and is discharged into the atmosphere. On the other hand, the feed gas stream supplied from tubing 14 is introduced into a flow path switchover device 100. The flow path switchover device 100 consists of a four-way valve having ports A, B, C, D, which are arranged to switch over the feed gas stream to a first condition having a flow path through ports A — C and D — B (shown by dotted lines) and to the second condition having a flow path through ports A — B and D — C (shown by solid lines).

In the first condition, the feed gas stream introduced into the flow path switchover device 100 via tubing 14 passes through the ports A — C, and into a combustion conduit 3 via tubing 24. The feed gas stream introduced into the combustion conduit 3 passes through the catalyst bed 7, and is introduced into the second flow path 9B of a continuous detector 9 via tubing 25, 27, ports D — B of the flow path switchover device 100 and tubing 28 and is discharged to the atmosphere. The tubing 25 adjoining the exit of combustion conduit 3 is provided with vertical branch tubing 26 and fitted with a valve 11 for discharging to the drain.

Next, when the flow path switchover device 100 is so actuated as to switch over the feed gas stream to said second condition, the feed gas stream supplied to the flow path switchover device 100 via tubing 14 flows into the second flow path 9B of the continuous detector 9 via ports A — B and tubing 28, being discharged into the atmosphere. At this time, supply of fresh feed gas to the combustion conduit 3 is stopped and the combustion conduit 3 is sealed by the tubing 24, 25, 26, 27, valve 11 and ports D — C of the flow path switchover device 100.

In such second step, a small amount of sample is injected into the combustion conduit 3 by a sample injector 8. Combustible materials in the injected sample react with oxygen contained in the feed gas inside the combustion conduit 3 in the presence of the catalytic action of the catalyst bed 7, consuming oxygen in an amount corresponding to the TOD of the sample.

Thereafter, by actuating the flow path switchover device 100 again so as to return the feed gas stream to the first condition, the gas inside the combustion conduit 3 participating in the combustion reaction is carried to the second flow path 9B of the continuous detector 9 via the tubing 27, ports D — B and tubing 28 by the feed gas stream caused to flow into said combustion conduit 3 via the tubing 14, ports A — C, tubing 24. The oxygen detector 9 generates an electrical signal corresponding to the difference in oxygen concentration between two gas flows of flow paths 9A and 9B. Therefore, when the gas inside the combustion conduit 3 participating in the combustion reaction reaches the second flow path 9B an electrical signal corresponding to the TOD of the sample is generated. Such electrical signal is recorded by recorder 10.

A further or fourth embodiment of the present invention becomes realizable by modifying the third embodiment of the present invention, by not dividing the feed gas stream supplied from the tank 1 into two paths, but using it only as a feed gas stream passing through the tubing 13 and 15, introducing the gas stream passing through the first flow path 9A of the oxygen detector 9 by the route shown by dotted lines into the port A of the flow path switchover device 100, and making the structure of the other parts the same as those shown in FIG. 3.

Next, a detailed explanation will be made with reference to the functional effects of the present invention.

In the conventional method, from the viewpoint of the ease of measuring and cost of the necessary apparatus, the TOD of the sample is determined from the amplitude of the electrical signal, particularly from the altitude of the recorded peak. In such a method, it is an indispensable condition in respect to precision measurement to carry out the injection and combustion of the sample and to carry the gas which is participating in the combustion to the oxygen detector with good reproducibility. In order to meet such conditions and to obtain precision measurements, it becomes important to carry out the injection and combustion of the sample and to carry the gas participated in the combustion reaction to the oxygen detector under respectively optimum conditions of the flow rate.

In the conventional method, several problems are brought about, because the combustion of the sample is carried out at a fast flow rate which is suitable to carry the gas participating in the combustion reaction to the oxygen detector. With reference to combustion of the sample, the combustible materials are unlikely to burn, because the combustible materials are veiled in an aqueous vapor which is a main component of the sample when the liquid drops of the injected sample evaporate. Also, because the vapor of the sample is transferred to the downstream side of the catalyst bed by the feed gas stream flowing inside the combustion conduit, enough combustion time cannot be provided. Accordingly, it is very difficult completely to oxidize the entire injected sample.

In spite of that, in the conventional method, the sample is burned inside the combustion conduit through which the feed gas stream flows at too fast a flow rate. Therefore, the time available for combustion is too short and part of the injected sample passes through the catalyst bed unburned. Accordingly, in the conventional method, as low as the oxidation ratio of the combustible materials is, a combustion reaction having high reproducibility is carried out by instantaneously and simultaneously oxidizing the injected sample. To do this, it becomes necessary to maintain the temperature of the combustion conduit at a high temperature of about 900°C, for example.

In order to provide momentary and simultaneous injection of the entire sample, in the conventional method, the entire amount of the weighed sample is injected as one spherical liquid drop. In such method, it is not infrequent that on account of a delicate difference as to finish of the tip of the injecting tube for the sample to be injected, the sample does not form a spherical liquid drop. Of, because the liquid drop may impinge upon the conduit wall of the combustion conduit, the results do not have a high degree of reproducibility.

And although depending upon the quality of a sample to be measured, by day and night continuous measuring for about a week, the internal wall and tip of the injecting tube are stained. Because of this a liquid drop is not formed, or it is divided into at least two drops, thus bringing about dispersion in the measured data. As such, it is very difficult to maintain the condition of momentary and simultaneous injection of the entire amount of the sample for a long period of time and it is problematical in respect of conservation of the apparatus. There is a further problem in that an inexpensive sample injector such as a microsyringe cannot be used, because it cannot perform a momentary and simultaneous injection of the entire amount of the sample.

Next, because the temperature of the combustion conduit is maintained at a high temperature of 900°C, the manufacturing and running costs of the apparatus are drastically increased and the lives of the electric furnace and combustion conduit become very short. And a problem in precision measuring is brought about since a part of water which is a main component of the sample decomposes or reacts in the presence of heat, generating oxygen which lowers the apparent TOD of the sample.

Further, in order to reduce as much as possible the error of measurement due to the low oxidation ratio of combustible materials, the conventional method makes it a rule to maintain strictly at constant values the flow rate and combustion temperature of the feed gas stream.

In order to overcome such deficiencies of the conventional method, the present invention carries out injection and combustion of the sample and carries the gas which is participating in the combustion reaction under respectively optimum conditions of the flow rate. Specifically, the sample is caused to burn sufficiently in a feed gas stream which is maintained under optimum conditions of flow rate for the combustion reaction and, after securing sufficient combustion time, the flow rate of the feed gas stream is increased and the gas contributed to the combustion procedure is carried to the oxygen detector under optimum conditions. By so doing, adequate combustion time may be secured, and moreover, the combustible materials contact the catalyst efficiently. Therefore, it is possible to oxidize the combustible materials in the sample almost completely, even at a combustion temperature below 900°C. Accordingly, when ($F_1$) is at an optimum, the entire amount of the weighed sample need not be momentarily and simultaneously injected at all, but the entire amount of the weighed sample may merely be injected into the combustion conduit. It goes without saying that no dispersion is brought about, even if the sample is divided into drops and injected, and the sample may be injected by use of a microsyringe. And, although depending upon the combustion time, the combustion temperature may be reduced to about 500°C. Therefore, it is possible to extend the lives of the electric furnace and of the combustion conduit, and moreover to reduce manufacturing and running costs. Further, because a high oxidation ratio is obtained, there is no necessity to pay attention to the maintenance of the analyzing conditions as strictly as in the case of the conventional apparatus.

When the concept of sealing the combustion conduit is adopted, movement of the feed gas inside the combustion conduit is stopped and the sample is injected and combustion reaction is completed in a sealed condition. Therefore the entire weighed sample need not be injected simultaneously or instantaneously but mere injection of the entire weighed sample into the combustion conduit easily suffices and maintenance of conditions for precision measurements becomes easy. And because the flow of the feed gas inside the combustion conduit has been stopped, there is no basis for fear that the vapor of the sample is carried irrespective of the state of completion of the oxidation reaction, and it becomes possible to allow sufficient time for the oxidation reaction. Therefore, it is possible to advance the oxidation reaction drastically as compared with known measuring apparatus.

Further, in contrast to the conventional troublesome method of determining the TOD from the difference of two values of electrical signals corresponding to the oxygen concentration of one gas stream, that vary as time passes, the present invention employs an oxygen concentration detector utilizing a single electrical signal corresponding to the difference between the oxygen concentrations of the two gas streams. Therefore, the TOD is determined easily from only one electrical signal.

Figure 4:
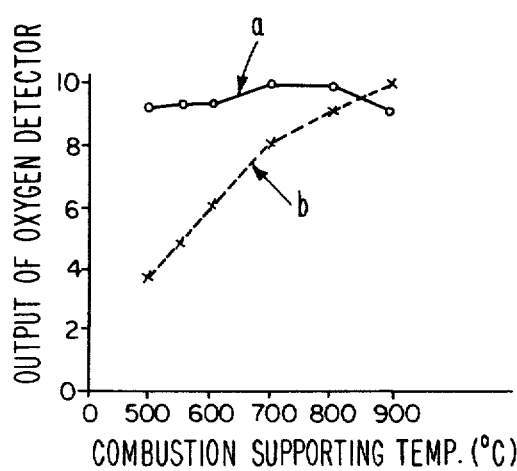
FIG. 4 is a graph showing the relationship between the combustion supporting temperature and the output of the oxygen detector, comparing this invention with the conventional method.

FIG. 4 compares the results of measuring samples of the same TOD concentration while varying the combustion temperature, using an apparatus according to the first embodiment of the present invention and by the conventional method, wherein curve (a) shows the results measured by an apparatus of the present invention and curve (b) shows the results measured by the conventional method. The flow rates of the feed gas stream in the apparatus of the present invention are $F_1$=10 cc/min and $F_2$=$F_3$=140 cc/min while the time during which the sample is maintained in said second step after its injection, namely the combustion time, is 30 seconds. The flow rate of the feed gas stream in the conventional method is 150 cc/min and the other conditions are the same as between the two processes. In FIG. 4, the output of the detector in the apparatus of the present invention hardly changes at all when the combustion temperature is reduced. However, the output in the conventional method is decreased in roughly a direct proportion. Further, in the apparatus of the present invention, even when the combustion temperature is drastically reduced, the sample can be burned substantially completely and the results of a high oxidation ratio are obtained by that proportion. Such effect is obtained, at least in part, as a result of contacting the feed gas stream with the vapor of the sample at a slow flow rate of about 1/5 of that of the conventional method, and by providing ample combustion time.

In FIG. 4, the output of the apparatus of the present invention reaches its maximum at about 700°C and the output lowers at temperatures higher than that at a temperature higher than about 700°C, combustion of the sample is carried out completely within 30 seconds and diffusion of the peak begins. The combustion time for making this output of the apparatus maximum can be altered by the combustion temperature or ($F_1$), especially by the value of the former, that is, as the combustion temperature is reduced, the combustion time should be increased.

Figure 5:
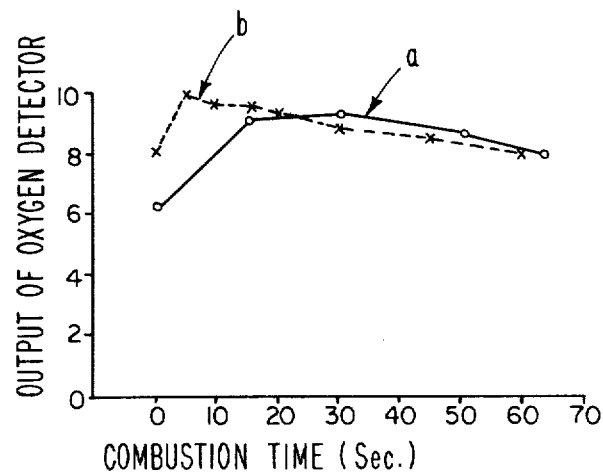
FIG. 5 is a graph showing the relation between combustion time and output of the oxygen detector.

Referring now to FIG. 5 of the drawings, this Figure shows the results of measuring samples of the same TOD concentration while varying combustion time, using the apparatus of the FIG. 1 embodiment of the present invention. Procedures using a combustion temperature of 600°C are shown by curve (a) and the case of a combustion temperature of 900°C is shown by curve (b). The measuring conditions are the same as the case of FIG. 4 except $F_1=5$ cc/min and $F_2=F_3=95$ cc/min.

In FIG. 5, when the combustion time is brief, the output of the oxygen detector is great when the combustion temperature is 900°C. However, when the combustion time exceeds 15 seconds, the outputs of the two become about the same. Namely, the data of FIG. 5 show that by increasing the combustion time, the same effect is obtained when the combustion temperature is 900°C or 600°C. Both these two curves have positions where the output of the oxygen detector becomes maximum. When the combustion time is longer than these, the output tends to reduce somewhat. This is because diffusion of the peak occurs after combustion of the sample has been carried out completely. The degree of diffusion becomes greater as the temperature becomes higher. Further, when the combustion temperature is as high as 900°C, the influence due to generation of oxygen due to thermal decomposition of water becomes non-negligible, which has something to do with the reduction of the output. However, when variation of the combustion time falls within the range of several seconds, the output of the oxygen detector in the vicinity of the maximum value, or during a combustion time above that, hardly changes. Accordingly, as long as measuring is carried out in these conditions, there is no need to control the combustion time strictly.

Figure 6:
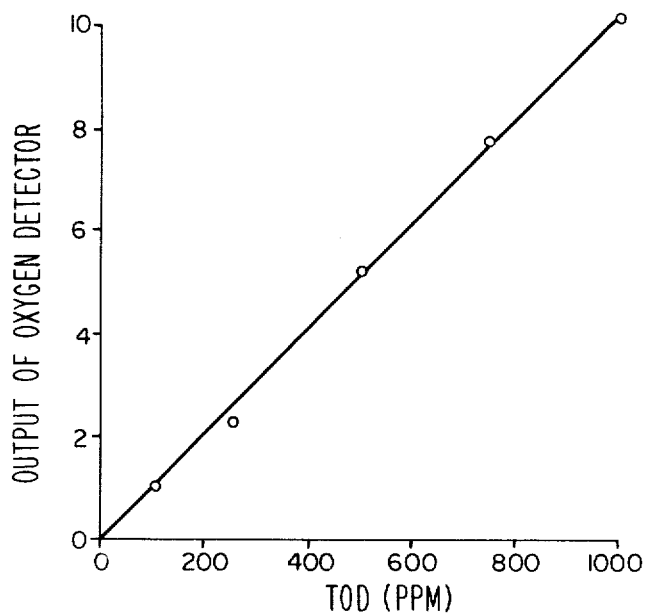
FIG. 6 is a graph showing the relationship between the total oxygen demand of the sample and the output of the oxygen detector when the combustion supporting temperature and combustion time are 550°C and 60 seconds, respectively.

FIG. 6 is a graph showing the relationship between the TOD of an aqueous dispersion of a known combustible material and the output of the oxygen detector, wherein the analyzing conditions include a combustion temperature of 550°C, a combustion time of 60 seconds, an $F_1=5$ cc/min and an $F_2=F_3=95$ cc/min.

The measurements relating to FIG. 4, FIG. 5 and FIG. 6 were obtained by using, as a feed gas, nitrogen gas containing 3,000 ppm of oxygen. The combustion chamber was a 17 mm $\phi$ × 350 mm quartz tube. The catalyst was a platinum net. The sample injector was a sliding plate valve and it was sent to measure and to inject 20 $\mu$l of sample.

In this embodiment, the conditions of analysis such as combustion time, combustion temperature and flow rate of the feed gas stream passing through the combustion conduit, especially the flow rate of the gas stream at the time of combustion, are mutually correlated. However, when they are measured roughly under the following conditions, good results are obtained.

The flow rate of the feed gas stream varies depending especially upon the shape and dimension of the combustion conduit, the shape and dimension of the gas flow path downstream of the catalyst bed and the combustion time. However, preferable results are obtained when the flow rate of the feed gas stream at the time of carrying a peak, namely, when the feed gas stream passing through the combustion conduit in said first step is flowing at 50 – 300 cc/min and the flow rate of the feed gas stream at the time of combustion of the sample in said second step is less than 1/5, preferably less than 1/10 of the flow rate in the first step.

Combustion time has an especially close relationship with the combustion temperature. As the combustion temperature is reduced, it is necessary to increase the combustion time. When a combustion time of 5 – 10 seconds is secured at a combustion temperature of 700 – 900°C and a combustion time of 10 – 20 seconds at a combustion temperature of 500 – 700°C is secured, preferred results are obtained.

The combustion temperature varies, depending upon the kind of catalyst used and the combustion time. However, preferred results are obtained when it is at least 400°C. Although it is possible to provide a high combustion temperature of at least 1000°C, this gives adverse effects in regard to manufacturing and running costs. Also, it tends toward the generation of oxygen due to thermal decomposition of water, and no particular effect is seen.

Figure 7:
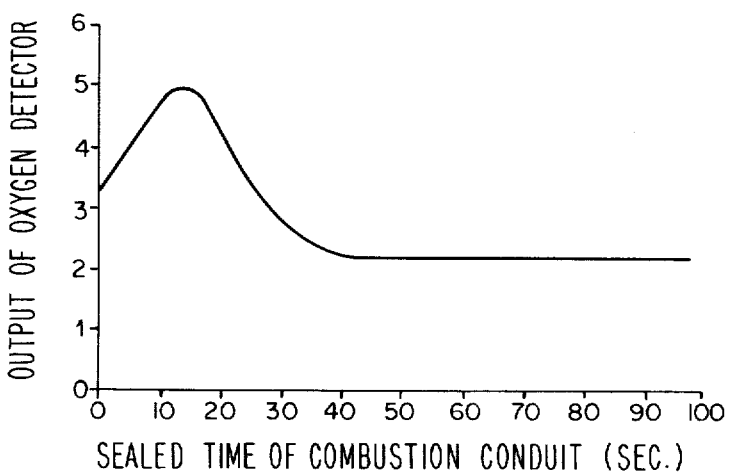
FIGS. 7 and 8 are graphs showing the results obtained in accordance with the embodiment of FIG. 2 of the present invention.
Figure 8:
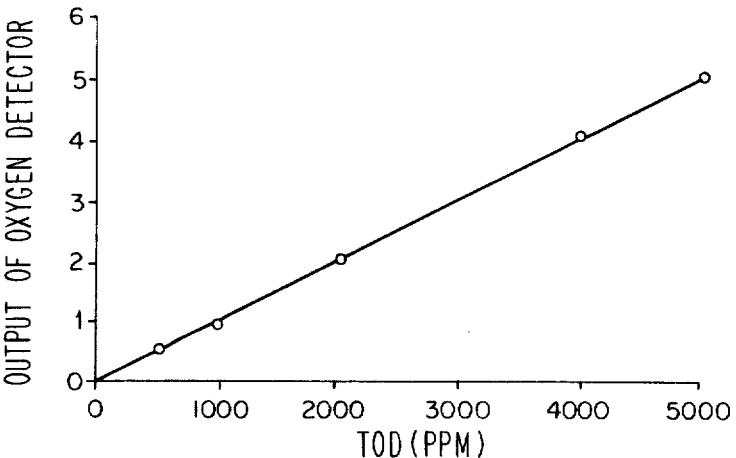

In order to explain in further detail certain other effects of the present invention, results measured by the procedure of the FIG. 2 embodiment of the present invention are shown by FIGS. 7 and 8.

The measuring method in this case used an inert gas containing 1.2% (by volume) of oxygen as the feed gas in FIG. 2, and we injected the sample by a microsyringe.

FIG. 7 shows the results of measuring the size of the output signal of the oxygen detector by varying the time during which the inside of the combustion conduit is sealed after the sample is injected with reference to samples of the same TOD concentration. In this case, an inert gas containing oxygen is used as the feed gas and oxygen in the feed gas is consumed for combustion. Since the change of oxygen concentration is large, a large electrical signal is obtained.

From FIG. 7, it will be understood that when the sealing time is long, the output signal becomes large, and the output reaches its maximum when the sealing time is not less than 5 seconds, preferably 10 – 20 seconds. When the sealing time is longer than that, the output signal gradually becomes small. However, when the sealing time is at least 60 seconds, the output signal does not change, even when the sealing time is varied. This fact shows that when the sample is injected at a sealing time of 0 seconds, namely, in which the feed gas stream flows inside the combustion conduit (conventional method), the oxidation ratio of the combustible materials is low. By sealing the combustion conduit for at least 5 seconds, preferably 10 – 20 seconds after the sample is injected, namely, by creating a combustion time of at least 5 seconds, preferably 10 – 20 seconds, the oxidation ratio of the combustible materials advances drastically. When the sealed condition is continued for more than 20 seconds, a zone is created in which the oxygen concentration of the feed gas decreases inside the combustion conduit. This is brought about by combustion and naturally diffuses inside the combustion conduit and inside all the tubing communicating therewith. Therefore, the output signal is lowered. When the sealed condition is continued for at least 60 seconds, such zone diffuses about uniformly. Therefore, the change of the size of the signal toward the sealing time becomes invisible. Accordingly, when the results in which the oxidation ratio of the sample is high and the output signal is large, are expected, a sample may be maintained in the second step immediately after the sample has been injected, namely for at least 5 seconds, preferably for 10 – 20 seconds, and it may thereafter be switched over the fist step. And when a stable output signal and a high oxidation ratio are required even if the output signal becomes somewhat smaller, the sealing time of the combustion conduit may be more than 60 seconds after the sample is injected.

Turning now to FIG. 8, this is a graph showing the relationship between the TOD of an aqueous dispersion of a known combustible material and the electrical output signal determined by injecting the sample in said second step and returning it to said first step within 60 seconds after the sample is injected in the apparatus of FIG. 2. In a known measuring apparatus of the same kind, from the use of a momentary, simultaneous injection of the entire sample, the measured results are not good with respect to reproducibility, when obtained by injection of the sample using a microsyringe. However, in this embodiment, good results as shown in FIG. 8 are obtained by injection using a microsyringe due to the aforesaid characteristics.

In the foregoing explanation of the embodiments of the present invention, injection of the sample is carried out by use of a microsyringe. However, in order to minimize the measurement error to the magnitude of the errors in weighing of the sample, and to advance the operability of the procedure, it is desirable to use an automatic sample injector. This becomes possible by connecting the injector to the sample inlet of the combustion conduit.

And, as a flow path switchover device, a four-way valve is adopted. However, so long as it is capable of switching over to a plurality of gas flow paths, any flow path switchover device may be used.

Figure 9:
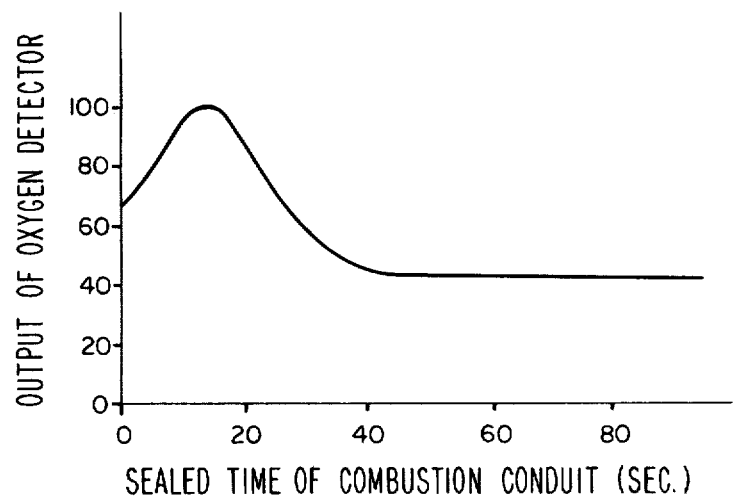
FIGS. 9 and 10 are graphs showing results obtained in accordance with the embodiment of FIG. 3 of the present invention.
Figure 10:
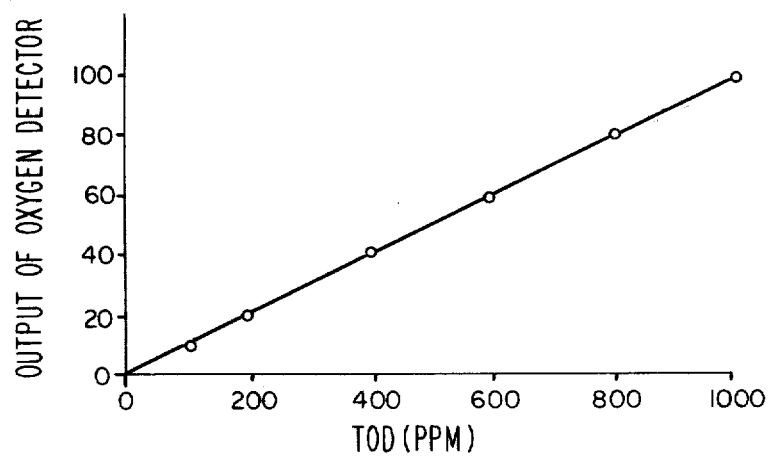

Further, the results measured by the third embodiment of the present invention are shown in FIGS. 9 and 10. FIG. 9 is a graph showing the results obtained in measuring the size of the output signal of the oxygen detector while varying the time during which the inside of the combustion conduit is sealed after the sample is injected with reference to samples of the same TOD concentration, and about the same results as in FIG. 7 are obtained.

FIG. 10 is a graph showing the relation between the TOD and the electrical output signal of a known sample determined by injecting the sample in said second step and returning it to said first step after 90 seconds after the sample was injected.

In the measurements of FIGS. 7 – 10, the oxygen concentration of the feed gas is maintained at 12,000 ppm, the flow rate of the feed gas is maintained at 150 cc/min, the temperature of the combustion conduit is maintained at 800°C and the amount of the injected sample is 40μl. And potassium hydrogen phthalate is used as the combustible material. A 17 mm φ × 350 mm quartz glass tube is used as the combustion conduit. The catalyst is platinum and the sample injector is a sliding plate valve or a microsyringe.

We claim:

1. In a method for determining the total oxygen demand of a combustible material in an aqueous dispersion, with the use of a heated combusion chamber in which a catalyst bed is located, and with the use of an oxygen detector which is connected downstream of said catalyst bed, the steps which comprise:
   a. supplying a feed gas stream composed of an inert gas containing oxygen at a constant rate into said combustion chamber in a manner to cause said stream to flow through said catalyst bed, and with the effluent gas from said bed flowing into said detector for determining the concentration of oxygen therein,
   b. dividing the stream in a manner to decrease the flow rate of said feed gas stream supplied into the combustion chamber to a flow rate that is lower than that of the step (a) and diverting the balance of the feed gas stream to said detector while bypassing said chamber,
   c. injecting a small amount of an aqueous dispersion of said combustible material into said combustion zone upstream of the catalyst bed while said flow rate of said feed gas stream is lower than that of step (a), whereby the combustible materials are burned in said gas, and
   d. increasing the flow rate of said feed gas stream in said chamber to substantially the same flow rate as in step (a), whereby an electrical signal corresponding to the total oxygen demand for burning the combustible materials is generated,
   the flow rate in step (b) being less than about 1/5 of the flow rate in step (a).

2. A method as described in claim 1, wherein said feed gas is air.

3. A method as described in claim 1, wherein said aqueous dispersion of the combustible materials is injected in a vaporous state.

4. A method as described in claim 1, wherein said inert gas is selected from the group consisting of nitrogen, helium amd argon.

5. A method as described in claim 1, wherein said catalyst is selected from the group consisting of asbestos, palladium, rhodium, nickel, platinum, cobalt, quartz fiber and silica gel.

6. A method as described in claim 1, wherein said catalyst is supported by a material selected from the group consisting of asbestos, glass fibers and quartz fibers.

7. A method for determining the total oxygen demand of combustible materials in an aqueous dispersion utilizing a detector of the type which determines the difference in oxygen concentration between two feeds, which comprises the following steps:
   a. providing a feed gas stream containing oxygen at a substantially constant rate, dividing said feed gas stream into two parts,
   b. supplying a first divided portion of said feed gas stream at a constant rate through a first flow path to one portion of said detector,
   c. supplying a second divided portion of said feed gas stream at a constant rate into a second circuit which is connected to a discharge through a second portion of said detector, said second circuit including a branch which leads into a combustion conduit in a combustion zone which is heated at a combustion supporting temperature, and which combustion zone products are connected to flow into said second portion of the detector, and said second circuit including another branch wherein the feed gas stream bypasses said combustion conduit in the combustion zone and then also flows into said second portion of the detector,
   d. decreasing the flow rate of the feed gas stream to said combustion zone to a value less than that of step (c), while bypassing the balance of said feed gas stream to a point downstream of said combustion conduit,
   e. injecting a small amount of an aqueous dispersion of combustible materials into the combustion zone upstream of the catalyst bed, whereby the combustible materials are burned, and
   f. increasing the flow rate of the feed gas stream to said combustion zone to the same flow rate as in step (c), whereby an electrical signal corresponding to the difference of total oxygen demand for burning the combustible materials is generated, the flow rate in step (d) being less than about 1/5 of that of step (c).

8. A method as described in claim 7, wherein said feed gas stream containing oxygen is air.

9. A method as described in claim 7, wherein said aqueous dispersion of combustible materials is injected in a vaporous state.

10. A method as described in claim 7, wherein said inert gas is selected from the group consisting of nitrogen, helium and argon.

11. A method as described in claim 7, wherein said catalyst is selected from the group consisting of platinum, cobalt, quartz fibers, silica gel, palladium and nickel.

12. A method as described in claim 7, wherein said catalyst is supported by a material selected from the group consisting of asbestos, glass fibers and quartz fibers.

13. An apparatus for determining the total oxygen demand of a combustible material in an aqueous dispersion which comprises:
   a. means for supplying at a substantially constant rate a feed gas stream composed of an inert gas containing oxygen,
   b. combustion conduit means forming a combustion zone having an inlet for introducing the feed gas stream into said combustion zone and an outlet for withdrawing the effluent gas stream from the combustion zone, said combustion zone including a heating means in which a combustion supporting catalyst bed is provided, and said combustion zone including an inlet for injecting the combustible material as an aqueous dispersion into the heating zone,
   c. means for connecting said feed gas stream to said combustion zone,
   d. bypass means for bypassing at least a portion of the flow of the feed gas stream to a location downstream of said combustion zone,
   said bypass including means for diverting at least a portion of the feed gas to a location downstream of said combustion conduit, whereby the combustible material may be injected into and burned in the combustion zone while the balance of the initial feed gas is introduced into the flow path downstream of said combustion zone, said bypass means being connected between the means for supplying the feed gas stream and the combustion conduit outlet,
   e. mixing means for causing the combustion products to flow downstream in admixture with the bypassed portion of the feed gas, and
   f. oxygen detecting means connected downstream of the mixing means and adapted to generate an electrical signal corresponding to the oxygen contained in the mixture passing therethrough.

14. An apparatus as described in claim 13, wherein said oxygen detecting means consists of a solid electrolyte tube including an oxygen concentration cell comprising a solid electrolyte having the property of conducting electricity purely by means of oxygen ions, and has two flow paths, one flow path connected to said means for supplying a feed gas stream, and the other flow path being connected to receive the mixture, whereby the oxygen detecting means generates an electrical signal corresponding to the difference in oxygen concentration between two gas streams passing through the two flow paths.

* * * * *